(12) United States Patent
Pulido et al.

(10) Patent No.: US 10,226,164 B2
(45) Date of Patent: *Mar. 12, 2019

(54) DENTAL SCANNER DEVICE

(71) Applicant: Apollo Oral Scanner, LLC, Miami, FL (US)

(72) Inventors: Alfonso Fernandez Pulido, Madrid (ES); David De Pablos Garcia, Madrid (ES)

(73) Assignee: Apollo Oral Scanner LLC, Miami, FL (US)

( * ) Notice: Subject to any disclaimer, the term of this patent is extended or adjusted under 35 U.S.C. 154(b) by 61 days.

This patent is subject to a terminal disclaimer.

(21) Appl. No.: 14/723,258

(22) Filed: May 27, 2015

(65) Prior Publication Data
US 2015/0250379 A1    Sep. 10, 2015

Related U.S. Application Data

(63) Continuation of application No. PCT/ES2012/070834, filed on Nov. 28, 2012.

(51) Int. Cl.
| | | |
|---|---|---|
| *A61B 1/00* | (2006.01) | |
| *A61C 9/00* | (2006.01) | |
| *A61C 13/00* | (2006.01) | |
| *A61B 1/24* | (2006.01) | |
| *A61B 1/247* | (2006.01) | |

(52) U.S. Cl.
CPC ............ *A61B 1/00172* (2013.01); *A61B 1/24* (2013.01); *A61B 1/247* (2013.01); *A61C 9/0053* (2013.01); *A61C 13/0004* (2013.01); *A61C 13/0019* (2013.01); *Y10T 29/49567* (2015.01)

(58) Field of Classification Search
CPC ......... A61C 1/088; A61C 5/14; A61C 9/0053; A61C 13/0004; A61C 13/0019; A61B 1/00172; A61B 1/00147; A61B 1/05; A61B 1/24; A61B 1/247; G01B 11/24; Y10T 29/49567
USPC ........................................................ 433/29
See application file for complete search history.

(56) References Cited

U.S. PATENT DOCUMENTS 4,575,805 A      3/1986  Moermann et al.
6,821,116 B2 *  11/2004  Severance .............. A61C 19/10
                                                                 433/26

(Continued)

FOREIGN PATENT DOCUMENTS

WO   PCT/EP2015/056694        10/2015

OTHER PUBLICATIONS

International Search Report for PCT Application No. PCT/ES2012/070834 dated Aug. 16, 2013.

(Continued)

*Primary Examiner* — Heidi M Eide
(74) *Attorney, Agent, or Firm* — Ted Whitlock

(57) ABSTRACT

The invention relates to a dental scanning device characterized in that it is essentially formed by two bodies, the first body or scanner body (1) housing a moving scan head (3) consisting of a longitudinal mobile element ending in the scanning head (4), and the second body or bite body (2) consisting of a casing for receiving the scanning head (4); in addition to the element that allows the patient to hold and position the device by means of the force or pressure exerted by the patient's bite.

6 Claims, 3 Drawing Sheets

(56) References Cited

U.S. PATENT DOCUMENTS

| | | | |
|---|---|---|---|
| 7,494,338 B2* | 2/2009 | Durbin | A61C 9/00 433/29 |
| 2002/0058229 A1* | 5/2002 | Sugimoto | A61B 1/247 433/29 |
| 2003/0049585 A1* | 3/2003 | Severance | A61C 19/10 433/29 |
| 2005/0019732 A1 | 1/2005 | Kaufmann et al. | |
| 2006/0154198 A1 | 7/2006 | Durbin et al. | |

OTHER PUBLICATIONS

English Translation of International Search Report for PCT Application No. PCT/ES2012/070834 dated Aug. 16, 2013.

Written Opinion for PCT Application No. PCT/ES2012/070834 dated Aug. 16, 2013.

English Translation of Written Opinion for PCT Application No. PCT/ES2012/070834 dated Aug. 16, 2013.

Logozzo, S., et al., A Comparative Analysis of Intraoral 3d Digital Scanners for Restorative Dentistry, The International Journal of Medical Technology, vol. 5, No. 1 (2011).

* cited by examiner

DENTAL SCANNER DEVICE

CROSS-REFERENCE TO RELATED APPLICATIONS

This is a continuation claiming priority to or the benefit of International Application No. PCT/US2012/070834 filed Nov. 28, 2012.

BACKGROUND OF THE INVENTION

A dental scanner device to be applied in general both in the field of stomatology, and dental prosthetics manufacturing.

More specifically, it is an intraoral dental scanner for 3D teeth and gingivae imaging through a corresponding visualizing device.

No manual manipulation whatsoever by an operator is necessary, as it is fully automated; it is introduced in the patient's oral cavity; the patient holds it by exerting pressure when biting it; therefore, the patient himself is the scanning fixed-reference system.

Teeth and gingivae 3D diagnostic and therapeutic images have been traditionally obtained by using replicas or models from alginate-impressed molds. Such replicas get gingiva and tooth negative images, which are later on converted into positive, and then scanned. However, these mainstream techniques pose a double problem: the patient is uncomfortable; and they are not very reliable and accurate; thus, the process is slow and costly.

There are several state-of-the-art devices that try to solve the problems posed by mainstream techniques; e.g.: panoramic dental X rays or computerized dental tomographies:

EP 0825837, "Modular intra-oral imaging system video camera", for instance, mainly provides a I-hand-held video camera to take images of the patient's inner part of the mouth. The camera has a socket; in the inner part of the socket there is a base, and a visualizing device, as well as a socket's long axis optically aligned sensor that converts into data the images taken by the camera.

US 2006154198 3D dental scanner is both an imaging method and a system to get images of the dental structure in the inner part of the oral cavity, through the motion of at least one image capturer set on an fixed-reference-system coupled arm, external to the mouth, to generate a 3D model of the structure, based on the images captured.

ES2 383 220, "Intraoral dental imaging sensor and X-ray system, using such sensor" is an intraoral dental radiological system equipped with a mouth-insertable x-ray imaging sensor. It is made up of an image-detection matrix to provide electronic signals. The system comprises a light source to receive the matrix-generated signals; it emits binary light impulses corresponding to a digital image to be transmitted; it also has a light receiver placed at a certain distance from the patient; it can detect a light modulation triggered by the light source; it can transmit to the image-treating device the signal corresponding to such modulation.

Lastly, ES2324658 (T3), "Laser-digitalizing system for dental applications" is a laser digitilizer that has a light source with collimation optics to generate a collimated light beam; a scanner optically coupled with the light source (configured to scan the collimated beam towards the object to be optically represented in a predetermined pattern); an imaging instrument with an optical axis in a e angle with the scanner; this is set up to detect a pattern reflection from the object, and generate the object surface representative data, based on the pattern reflection; and a scanner-coupled processor, and [Sic.] the imaging system, configured to render a data-based 3D image of the object; it is characterized by the fact that the scanner is set up to scan the collimated beam all along at least to axes in the predetermined pattern. Such pattern encompasses a series of curvilinear segment".

These state-of-the-art devices and systems have several inconveniences. First, in some cases, a technician must manually operate them with a toothbrush-like motion, which, obviously, is inaccurate. Likewise, they are based on photographs taken by the various devices; usually, a software interprets and interpolates such photographs to take a final 3D image. Thus, besides the time needed to get the final image, these known systems depend on the operator's skill for manipulating the camera and inserting it in not-easy-to-reach parts of the mouth. Other known devices do not depend so much on manual operation, but have an external fixed-coordinate system, independent of the patient; therefore, the final image is exclusively based on the images captured with no extra projection; thus, they are not very accurate, as the reference system changes with the slightest movement of the patient.

BRIEF SUMMARY OF THE INVENTION

This invention is a dental scanning device without any of the flaws of the previously known state-of-the-art systems; it captures 3D images with respect to a fixed-reference system, i.e., the patient's mouth; thus, images are accurate, as the device moves along with the patient, i.e., teeth-position point of reference, for instance, as related to the device, is preserved at all moments, and remains in place while scanning.

To do so, this dental scanning device is made up of two embodiments; one of them lodges the scanner as such, as well as a mobile head probe; the other one is to be held when the patient bites, and is to correspondingly house the mobile head probe. Once the head probe part is introduced in the bite fixture—and therefore is held by the patient's mouth-the head probe sweeps in at least two directions. One, following the long axis of the head probe; and the other one, perpendicular to it, in both senses of the same direction, so that scanning is the result of a combination of both movements: lateral and deep, as related to the dental arch. This is why the embodiment to be held by the patient's mouth is made of an easy-to-disinfect/sterilize material.

Optionally, the aforementioned embodiments can be coupled to one another, and may be disassembled and joined again; in this case, either the patient's mouth-held piece is made of an easy-to-disinfect I sterilize material, or is disposed after use. In this case, the scanning embodiment (1) and the bite fixture (2) area easily coupled to one another through specially placed devices in the coupling ends.

Below there is a description of the invention, based on one of the versions of choice, and as per attached drawings.

DETAILED DESCRIPTION OF THE INVENTION

Figure 1:
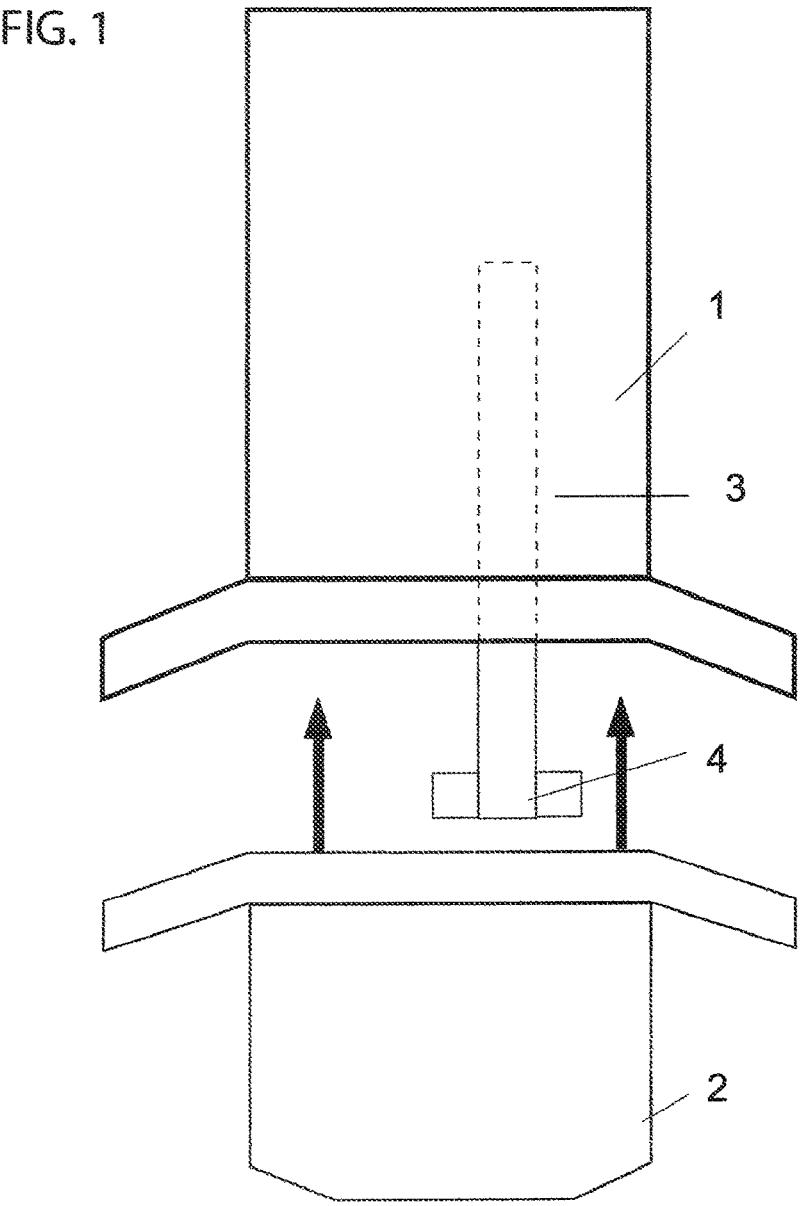
FIG. 1: Scanner device as per one version of the invention, as seen from above.

As shown in FIG. 1, the dental scanner is made up of two embodiments. The first one, the scanning embodiment, lodges a mobile scan head probe (3) on a mobile long element at the end of which is the scan head probe (4) as such. This mobile element (3, 4) is partially kept inside the scanner embodiment (1). On the other hand, the scanner head probe (4) juts out the embodiment (1) and is lodged in the second embodiment or bite fixture (2) by way of a pocket. Thus, the bite fixture (2) is, therefore, a scanner head probe lodging pocket (4).

In case the abovementioned bodies can be coupled, and separated and coupled again, the above is equally applied, just as when both embodiments (1 & 2) have been previously coupled to one another.

As indicated, the bite fixture (2) is introduced in the patient's mouth; and it is held in place when the patient bites it, so that the scanner head probe (4) is introduced in the mouth to scan the corresponding dental arch.

Likewise, the bite fixture (2) is mouth shaped to make it easier to hold. Such bite fixture (2) is basically a protective pocket for the scanner head probe (4), and can be bitten by the user. This is why the bite fixture (2) is made of a suitable transparent material.

Figure 2:
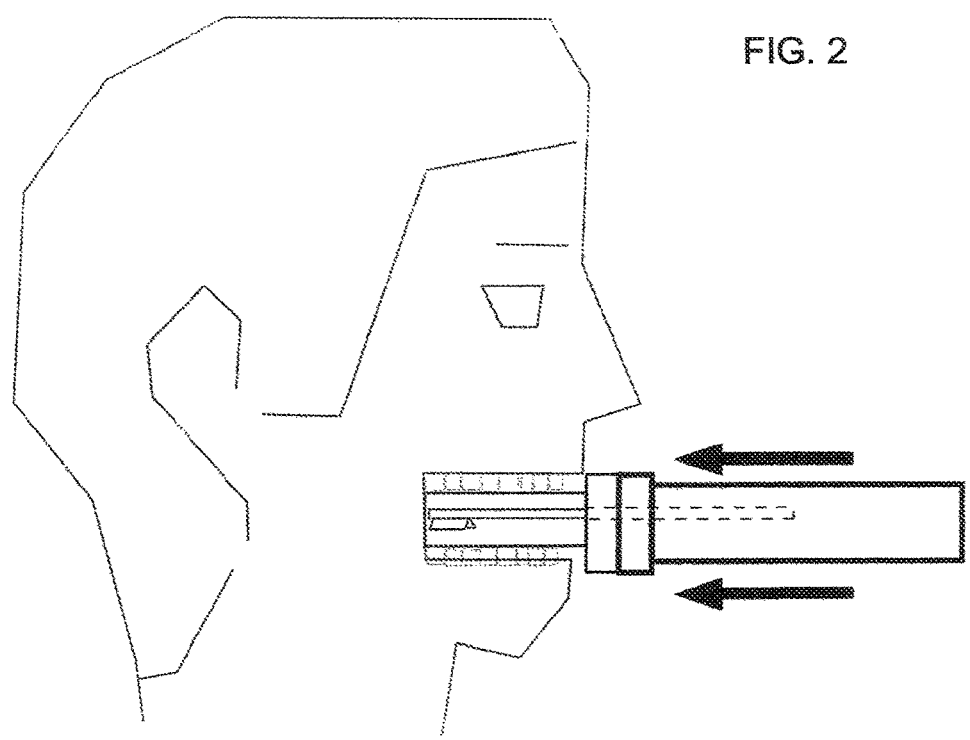
FIG. 2: Side view of the scanner device in FIG. 1, showing how it is placed in the patient's mouth.
Figure 3:
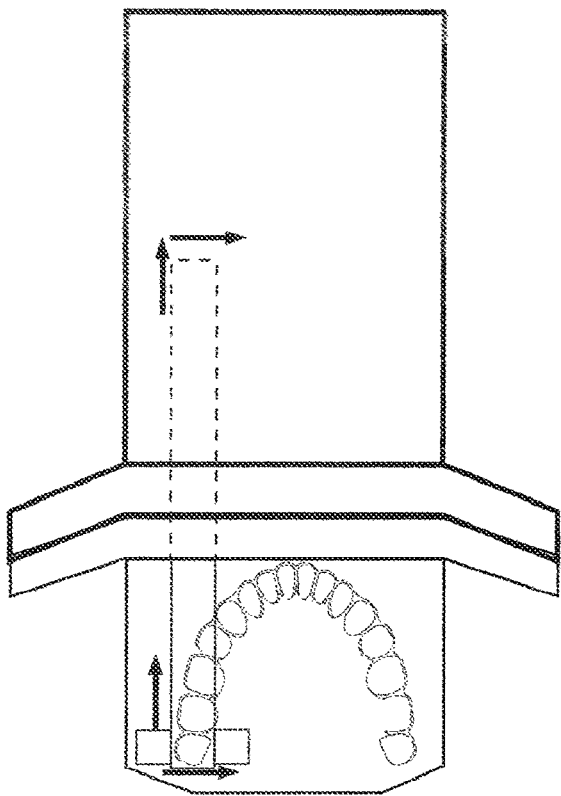
FIG. 3: Schematization of FIG. 1, showing device scanning directions.

Once the part of the scanner head probe (4) that is housed in the bite fixture (2) is introduced (reason for which it is secured in the patient's mouth), as shown in FIG. 2, the scanner head probe sweeps all along in at least two directions; one following the long axis of the long element (3), while the other one goes perpendicular to it in both directional senses, in such a way that scanning is the result of combining both side and deep motions with regard the dental arch, as shown in FIG. 3.

For the intraoral scanning, the device includes detection sensors, laser sensors or similar devices in the scanner head probe (4), as well as cameras to capture tooth-by-tooth sweep images from the dental arch and gingivae. These are automatically generated and exact 3D images, as a result of their fixed and constant reference system.

The invention claimed is:

1. A dental scanner device for 3D teeth and gingivae imaging, said device comprising a scanner housing, which houses an elongate mobile element which juts out the housing and ends in a scanner probe head, the scanner probe head comprising an element for emitting scanning energy, and wherein the mobile element ending in the probe head moves within a bite fixture along a long axis of the mobile element and perpendicular thereto, the bite fixture being held by the patient when biting said bite fixture during a dental scan procedure wherein the scan procedure is fully automated and generates a 3D image of the dental arch and gingivae wherein the housing, mobile element, scanner probe head, and bite fixture forming the device can move with the patient's mouth, the patient's mouth being a fixed point of reference for the scan procedure, and thereby preserving the fixed point of reference at all moments while scanning.

2. The dental scanner device of claim 1, wherein the bite fixture comprises a transparent material through which a scan can be performed.

3. The dental scanner device of claim 1, wherein the bite fixture is capable of being coupled to and separable from the scanner housing.

4. The dental scanner device of claim 1, wherein the bite fixture is disposable.

5. The dental scanner device of claim 1, wherein the device is portable and capable of being hand-held by the patient during the scanning procedure.

6. A method for scanning a dental arch comprising the steps of:
   a) providing a dental scanner of claim 1;
   b) placing the bite fixture in a patient's mouth; and
   c) performing a scan to produce a three-dimensional image of the dental arch.

* * * * *